(12) United States Patent
van Sloten et al.

(10) Patent No.: US 7,195,612 B2
(45) Date of Patent: Mar. 27, 2007

(54) ESOPHAGEAL BALLOON CATHETER WITH VISUAL MARKER

(75) Inventors: Leonard A. van Sloten, Groningen (NL); Cornelius van Wee, Drachten (NL)

(73) Assignee: Gordis Corporation, Miami Lakes, FL (US)

( * ) Notice: Subject to any disclaimer, the term of this patent is extended or adjusted under 35 U.S.C. 154(b) by 0 days.

(21) Appl. No.: 11/119,259

(22) Filed: Apr. 29, 2005

(65) Prior Publication Data

US 2006/0224114 A1    Oct. 5, 2006

Related U.S. Application Data

(63) Continuation-in-part of application No. 11/095,948, filed on Mar. 31, 2005.

(51) Int. Cl.
*A61M 29/00* (2006.01)
*A61M 31/00* (2006.01)
*A61M 37/00* (2006.01)

(52) U.S. Cl. .................................... 604/103.1

(58) Field of Classification Search ........ 604/509–510, 604/96.01, 103.06–103.09, 103.13–103.14, 604/523–528, 103.1, 63.1, 529; 600/116
See application file for complete search history.

(56) References Cited

U.S. PATENT DOCUMENTS

| 4,195,637 | A |   | 4/1980  | Gruntzig et al. |
|-----------|---|---|---------|-----------------|
| 4,723,936 | A |   | 2/1988  | Buchbinder et al. |
| 4,798,586 | A | * | 1/1989  | Stevens .................... 604/96.01 |
| 4,881,547 | A | * | 11/1989 | Danforth ..................... 606/194 |
| 5,217,440 | A | * | 6/1993  | Frassica ...................... 604/524 |
| 5,338,301 | A |   | 8/1994  | Diaz |
| 5,496,292 | A |   | 3/1996  | Burnham |
| 6,468,244 | B1 |  | 10/2002 | Leone et al. |
| 6,761,708 | B1 | * | 7/2004 | Chiu et al. .................. 604/265 |
| 2004/0015052 | A1 | * | 1/2004 | Barthel ........................ 600/116 |
| 2004/0267195 | A1 | * | 12/2004 | Currlin ..................... 604/103.1 |

* cited by examiner

*Primary Examiner*—Catherine S. Williams
(74) *Attorney, Agent, or Firm*—Michael W. Montgomery

(57) ABSTRACT

A balloon catheter for use with an endoscope may have a flexible shaft extending between a proximal and distal end, with a hub affixed to the proximal end, and a balloon that has one or more visual markers. An additional optional feature is that the markers(s) may be color-coded.

16 Claims, 3 Drawing Sheets

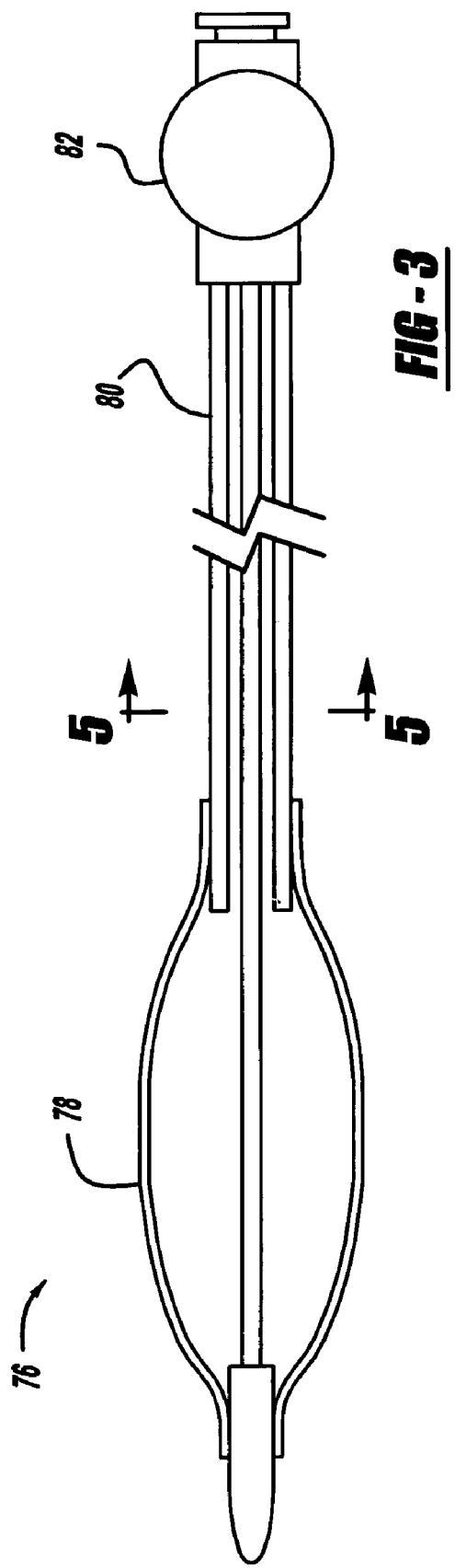
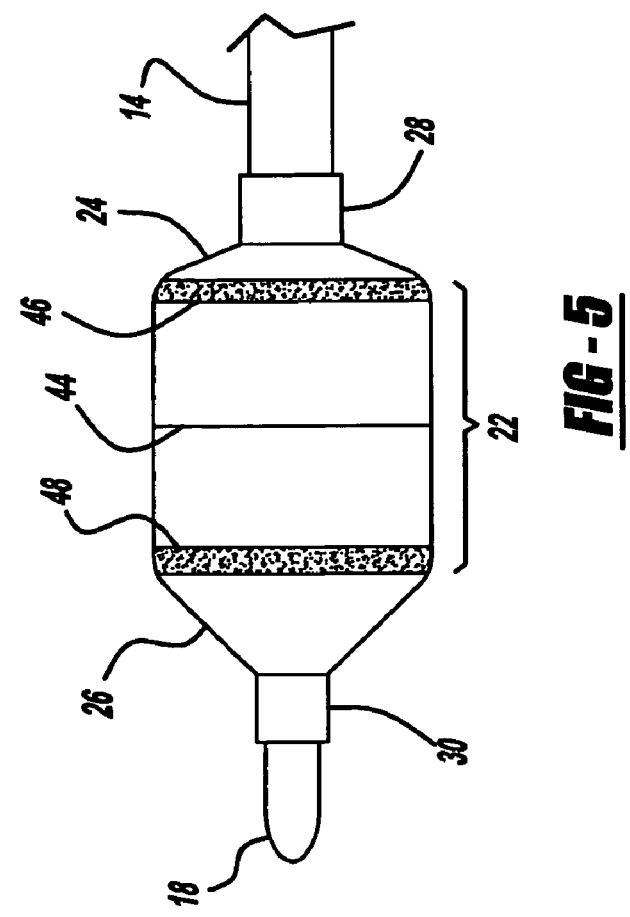
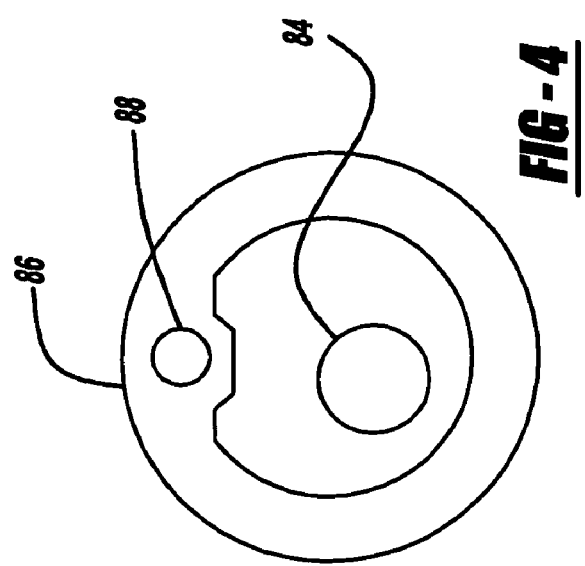
FIG-3
FIG-4
FIG-5

ESOPHAGEAL BALLOON CATHETER WITH VISUAL MARKER

CROSS-REFERENCE TO RELATED APPLICATION

The present application is a continuation-in-part of Ser. No. 11/095,948 entitled "Esophageal Catheter With Asymmetrical Balloon" filed Mar. 31, 2005.

BACKGROUND AND SUMMARY OF THE INVENTION

1. Technical Background

The present invention relates generally to medical devices, and more particularly to a balloon catheter having at least one visual marker for use with an endoscope.

2. Discussion

There are many different kinds and types of balloon catheters, including for example angioplasty catheters, stent delivery system catheters, etc.

By way of example, the present invention will be described in relation to an esophageal balloon catheter. However, it should be understood that the present invention relates to any balloon catheter having the features recited in any one of the following claims, and is not limited to any particular treatment such as esophageal use, or use with an endoscope, or the particular example embodiments described below.

Balloon catheters often have a relatively flexible tubular shaft having a certain length, which defines one or more tubular passages or "lumens" extending through part or all of the catheter shaft, and has an inflatable balloon attached near one end of the shaft. This end of the catheter where the balloon is located is customarily referred to as the "distal" end, while the other end is called the "proximal" end. The proximal end of the shaft is generally coupled to a hub, which defines an inflation port for connection to an inflator for selectively applying pressure to a fluid inflation medium, thus inflating the balloon. Structurally, the inflation port leads to an inflation lumen defined by the shaft, which extends to and communicates with the interior of the balloon, for the purpose of selectively inflating and deflating the balloon.

When a catheter includes a lumen adapted to slidingly receive a guidewire, it is referred to as a "guidewire lumen," and it will generally have a proximal and distal "guidewire port." The distal guidewire port is often at or near the catheter shaft distal end.

A guidewire has a flexible wire-like structure extending from a proximal end to a distal end. The guidewire will usually be of a size selected to fit into and slide within a corresponding guidewire lumen of a catheter.

If a balloon catheter includes a hub affixed to the catheter shaft proximal end, the hub may serve a variety of functions. Such functions may include providing a handle for manipulating the catheter, and/or defining proximal port(s) communicating with lumen(s) defined by the catheter shaft. When there is a guidewire lumen defined by a catheter shaft, its proximal guidewire port may be defined by a proximal hub, referred to as an "over-the-wire" catheter; or the proximal guidewire port may be located at some point along the sidewall of the catheter shaft, referred to as a "rapid exchange" catheter.

When a catheter has no guidewire lumen, but instead has a flexible wire or wire-like distal extension affixed to the catheter, it may be referred to as a "fixed wire" catheter.

Whether a particular catheter has a guidewire lumen or has a fixed-wire design, the guidewire or fixed-wire is intended to allow the catheter to more easily select and steer along a desired path.

In a fixed wire balloon catheter, a wire or wire-like structure may simply be attached to the distal end of the balloon catheter. Alternately, a flexible wire or wire-like structure may be affixed to the proximal hub, extending from the proximal end of the catheter, though the shaft and the balloon (perhaps in a dedicated lumen), and may extend a relatively short distance distal of the balloon. In another possible configuration, a distal extension of an inner body of the catheter shaft may serve as a "fixed wire" guiding element.

In general, balloon catheters according to the present invention may have one or more of the following features: (i) a balloon that has at least one visual marker; (ii) which may be color coded.

In greater detail, one or more visual markers may be provided on the balloon material or in the balloon material itself. Such visual markers may assist a physician to accurately position the balloon. In the case where a balloon catheter is used with an endoscope, the marker may be viewed visually with the endoscope, by using the endoscopic lens to look through the balloon material of the proximal tapering portion. In other words, the physician's view is provided by an endoscope positioned proximal of the balloon, yet the physician can look through the translucent material of the balloon proximal tapering portion, and see the interior surface of a cylindrical working portion to visualize where the marker(s) is from the "inside."

Such a visual marker may have any suitable shape or arrangement, including a circumferential band placed at the longitudinal center of the balloon, or a marker placed at one or both of the transitions between a central working portion and the proximal and distal tapering portions. Such markers may enable a physician to use the view through an endoscope to accurately position the balloon at the desired site for treatment, for example centered within a lesion or stricture. Of course, various combinations of these marker arrangements may be used.

In another optional additional feature, the marker(s) may be color-coded. For example, a marker of a particular color may indicate certain properties, such that the catheter balloon is of a particular size, allowing a physician to quickly confirm that the desired size balloon has been selected for use. Visual markers may also be made of different sizes or patterns, to indicate balloon catheter properties.

Another possible option is that the markers may be combination markers, which can be seen not only with visible light using an endoscope, but also with at least one additional viewing system, such as for example x-ray fluoroscopy, magnetic resonance imaging, etc.

In the case of a balloon catheter for use with an endoscope, the balloon material may be translucent, to allow a physician to use the endoscope to look through the balloon material at the anatomy, so the physician can accurately position the balloon. In addition, the proximal tapering portion of a translucent balloon may have a relatively steep tapering angle, to enhance the clarity of the picture presented to the physician by the endoscope.

Again in the case of a balloon catheter for use with an endoscope, after or during a therapeutic procedure, a physician may wish to retract the balloon catheter back into a passage or lumen defined by the endoscope. Another example may be a balloon catheter for use with a guiding catheter which defines a lumen. During such retraction into an endoscope or guiding catheter, the balloon material of some balloon catheters may possibly "bunch up" toward the distal direction as the balloon catheter is withdrawn back into such a passage or lumen, which may make retraction difficult.

Accordingly, another possible feature of a balloon catheter may be a balloon having a distal tapering portion with a relatively shallow tapering angle, so as to facilitate retraction of the balloon catheter back into an endoscope. The resulting gradual change in distal balloon size may tend to cause the balloon material to more easily fold or pleat and reenter a passage defined by the endoscope, thus reducing retraction force.

Another possible feature may be high pull strength, which may include a catheter shaft of a balloon catheter with reinforcement, such as reinforcing braid or strand(s). The resulting stronger catheter shaft will thus exhibit low longitudinal elongation under stress. Accordingly, if retraction becomes difficult, such reinforcing element(s) will tend to resist elongation of the catheter shaft.

An optional additional feature may be an asymmetrical balloon with a cylindrical working portion, flanked by proximal and distal tapering portions, which are in turn flanked by proximal and distal balloon legs, which are affixed to the catheter shaft. A possible feature of a longitudinally asymmetrical balloon is having proximal and distal tapering portions that taper at different angles.

This disclosure of the present invention will include various possible features and embodiments. However, the present invention scope as set forth in each of the claims, and is not limited to the particular arrangements described in this disclosure.

The terms "tube" and "tubular" are used in their broadest sense, to encompass any structure arranged at a radial distance around a longitudinal axis. Accordingly, the terms "tube" and "tubular" include any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; or (vi) has any desired combination of length or cross-sectional size.

Any suitable material may be used to make the components described, including polymers, metals and other materials suitable for use with medical devices.

It is of course possible to build various kinds and designs of catheters according to the present invention, by various techniques and of various materials, to obtain the desired features. It should be noted that the present invention also relates to methods for making and using a balloon catheter, in addition to the balloon catheter itself.

These and various other objects, advantages and features of the invention will become apparent from the following description and claims, when considered in conjunction with the appended drawings. The invention will be explained in greater detail below with reference to the attached drawings of a number of examples of embodiments of the present invention.

BRIEF DESCRIPTION OF THE DRAWINGS

FIG. 3 is a longitudinal cross-section view of a balloon catheter;

FIG. 4 is a transverse cross-section view of the balloon catheter of FIG. 3; and FIG. 5 is a partial side elevation view of a balloon catheter.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
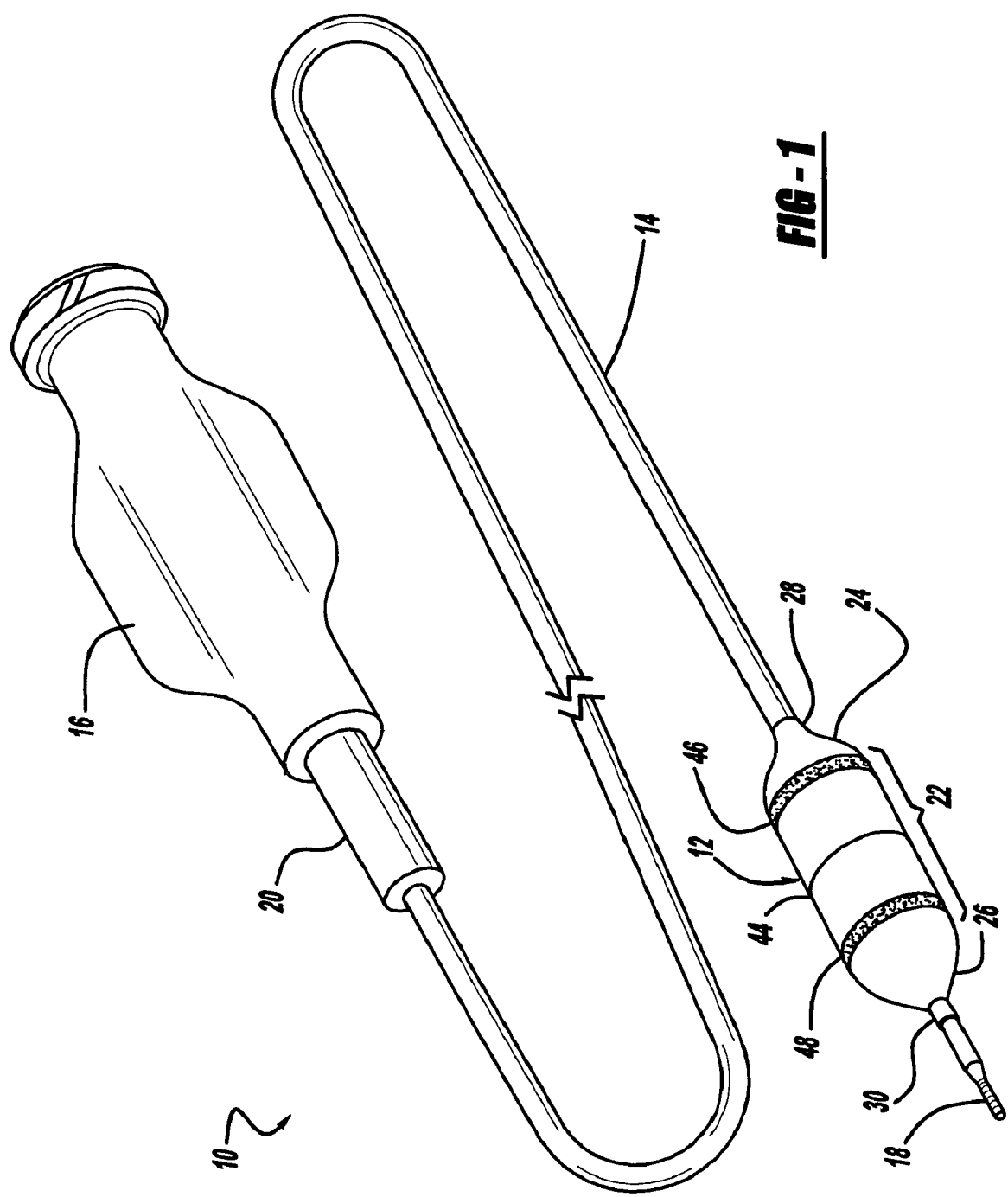
FIG. 1 is a perspective view of a balloon catheter.

The drawings depict a variety of balloon catheters and various features. FIG. 1 shows a balloon catheter 10 having a balloon 12, a flexible shaft 14, and a hub 16. The shaft 14 has a proximal and distal end, with the balloon 12 being attached to the shaft 14 near the distal end, and the hub 16 attached to the shaft 14 near the proximal end. A distal tip element 18 is affixed to the shaft 14 at the distal end, and a strain relief 20 is positioned at a transition between the shaft 14 and the hub 16. Balloon 12 has a cylindrical working portion 22, flanked by a proximal and distal tapering portion 24 and 26, which are in turn flanked by a proximal and distal balloon leg 28 and 30.

In addition, balloon catheter 10 has some visual markers on the material of the balloon 34. In the specific example shown in FIG. 1, the balloon 12 has a central marker 44 that encircles the longitudinal center of the balloon, as well as a pair of markers 46 and 48 which indicate the proximal and distal extent of a working portion of the balloon. The visual markers may be of various sizes, colors, and arrangements. In the example shown in FIG. 1, markers 46 and 48 are wider than central marker 44. In one possible example, markers 46 and 48 may be spaced approximately 2.5 cm from the central marker 44.

When balloon catheter 10 is used with an endoscope, markers 44, 46 and 48 may be seen from the "outside" when the balloon 12 is deflated, and from the "inside" when the balloon 12 is inflated.

An optional additional feature is that the markers may be color-coded. For example, a marker of a particular color may indicate certain properties, such that the catheter balloon is of a particular size, allowing a physician to quickly confirm that the desired size balloon has been selected for use. Visual markers may also be made of different sizes or patterns, to indicate balloon catheter properties.

Of course, a variety of markers and indicators of various configurations may be used, including lines, arrows, circles, text, triangles, pointers, etc.

Another possible option is that the markers may be applied or made using a variety of materials and techniques. Markers may be applied to the balloon's outer surface or inner surface, or if the balloon has more than one layer of material, the markers may be present between layers of the balloon. The marker material may be any suitable material, including ink, pigment, or paint, and may be applied using spray, adherence, shrink wrap, applications, or extrusion technologies.

Another possible option is that the markers may be combination markers, which can be seen not only with visible light using an endoscope, but also with at least one additional viewing system, such as for example x-ray fluoroscopy, magnetic resonance imaging, etc.

Figure 2:
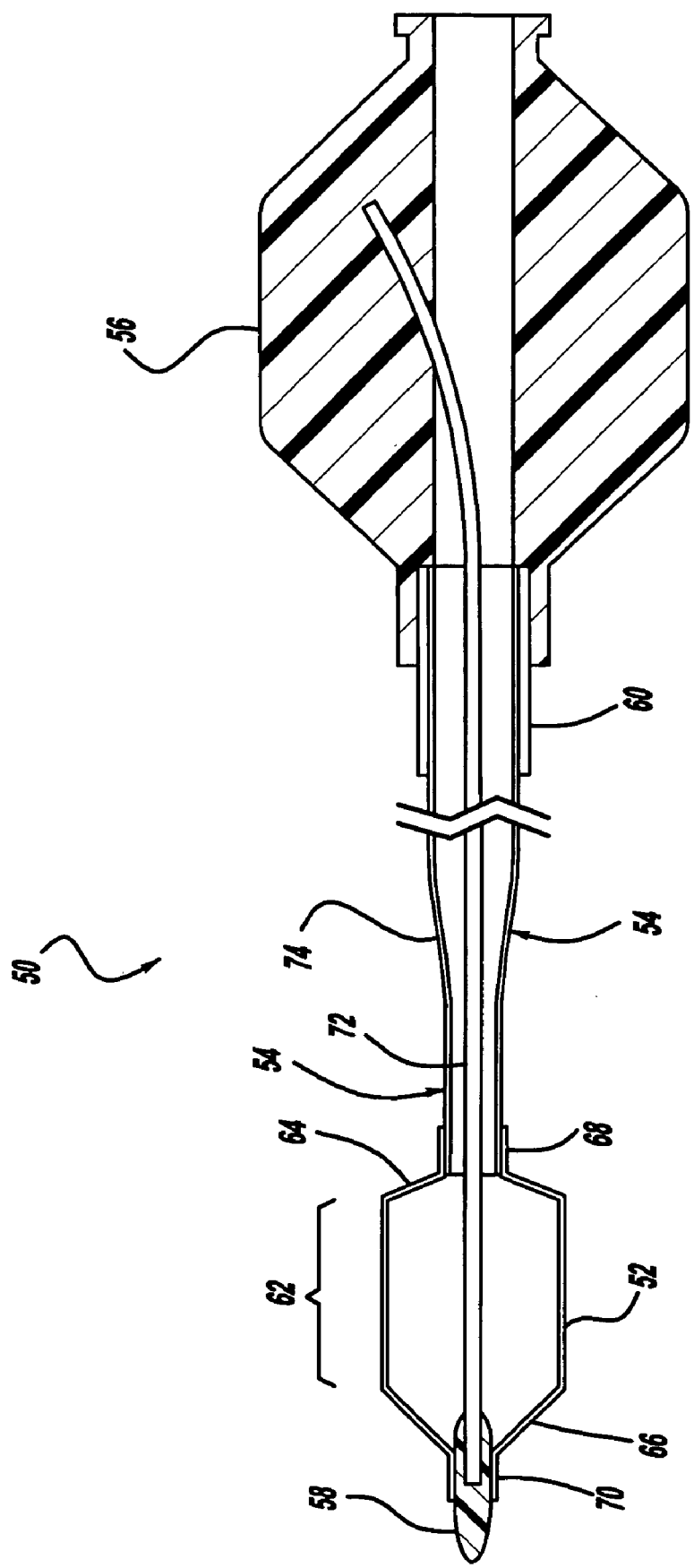
FIG. 2 is a longitudinal cross-section view of a balloon catheter.

FIG. 2 shows a balloon catheter 50 having a balloon 52, a flexible shaft 54, and a hub 56. The shaft 54 has a proximal and distal end, with the balloon 52 being attached to the shaft 54 near the distal end, and the hub 56 attached to the shaft 54 near the proximal end. The hub 56 defines an inflation port in fluid communication with an inflation lumen defined by the shaft. A distal tip element 58 is affixed to the shaft 54 at the distal end, and a strain relief 60 is positioned at a transition between the shaft 54 and the hub 56. Balloon 52 has a cylindrical working portion 62, flanked by a proximal and distal tapering portion 64 and 66, which are in turn flanked by a proximal and distal balloon leg 68 and 70.

In the illustrated example, the proximal and distal tapering portions 64 taper at different angles, with the proximal tapering portion 64 tapering at a much steeper angle than distal tapering portion. For example, one arrangement of a balloon catheter may include a shallow distal tapering angle of approximately 45 or 50 degrees with respect to a longitudinal axis, while the proximal tapering angle may be as close to perpendicular as possible, for example within approximately 10 degrees of perpendicular.

The flexible shaft 54 of FIG. 2 includes an inner member 72 and an outer tubular body 74. Inner member 72 extends from the hub 56 to the distal tip element 58, and may have high pull strength to serve as a reinforcing wire. The resulting stronger catheter shaft will thus exhibit low longitudinal elongation under stress. The proximal and distal ends of inner member 72 may be affixed to the hub 56 to the distal tip element 58 by any suitable means, including heat sealing, injection molding, and an adhesive. Of course, inner member 72 may be made of various materials having the desired properties, including stainless steel.

FIGS. 3 and 4 show partially diagrammatic views of a balloon catheter 76 having a similar arrangement, including a balloon 78, a flexible shaft 80, and a hub 82. The shaft 80 in this example has an inner member or stiffening wire 84, and a tubular outer body 86. Outer body 86 also has at least one integral wire 88 extending within the wall of outer body 86, which may be stainless steel, or Kevlar or Dyneema fiber another material having high pull strength and low elongation under stress.

A larger view of a distal segment of a balloon catheter is shown in FIG. 5, including a shaft 14 and distal tip 18, a balloon having a cylindrical working portion 22, and a proximal and distal tapering portion 24 and 26, and proximal and distal legs 28 and 30. The balloon also has a central marker 44 which encircles the longitudinal center of the balloon, as well as a proximal and distal marker 46 and 48 which extend around the circumference of the balloon at the proximal and distal ends of the central working portion 22.

Balloon catheters according to the principles of the present invention may be made of any suitable material using a variety of methods. Various polymers have the desired characteristics of strength, resilience, flexibility, biocompatibility and endurance. Many different materials may be used for manufacturing steerable catheters of the present invention. For example, some of the polymer materials may include polyamides, polyurethanes, nylons, polyethylenes, including high-density polyethylene (HDPE), polyether block amide (PEBA) which is available as Pebax®, polyester (PET), polycarbonate, polypropylene, acrylonitrile-butadiene styrene terpolymer (ABS), or polyetheretherketone (PEEK). Also, any of the catheter components may be made of a co-extrusion or a blend or a block copolymer of such polymer materials.

Many variations on components and designs of a balloon catheter are possible. For example, a reinforcing element may be included using another material, such as Kevlar or Dyneema (HDPE) fibers. Alternately, reinforcing member(s) may be embedded in the wall of the outer body, and may include a single wire or fiber, or may include multiple fibers which may be braided or coiled about the outer body.

EXAMPLE

An example balloon catheter may be constructed, including a nylon balloon, nylon tubular outer body, a stainless steel inner member and a stainless steel wire embedded in the wall of the outer body. The wire may for example have a diameter of 0.2 mm, which can reduce elongation of the shaft to less than 1 mm per meter of catheter length, when a pull force of about 20 N is exerted. A visual marker may be positioned on the balloon material at a longitudinal center of the balloon, and other markers may be positioned 2.5 cm proximal and distal of the center marker.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A balloon catheter fair use with an endoscope, comprising:

a flexible shaft having a proximal end and a distal end; the shaft defining an inflation lumen;

a balloon defining an interior and being made of translucent balloon material which is substantially inelastic; the balloon having an inflatable portion extending between a proximal and distal balloon portion, each proximal and distal balloon portion being affixed to the catheter shaft; the balloon having at least one visual marker;

wherein the balloon is affixed to the catheter shaft near its distal end; and the inflatable portion includes a cylindrical working portion arranged between a proximal and distal tapering portion; the balloon in an initial configuration being deflated, pleated and wrapped around the catheter shaft;

wherein visual markers are positioned at a longitudinal center of the balloon and at proximal and distal ends of the cylindrical working portion of the balloon; and wherein the central visual marker is thinner than the markers at the proximal and distal ends of the cylindrical working portion;

a hub affixed to the proximal end of the shaft and defining at least an inflation port; such that the inflation lumen communicates between the inflation port and the balloon;

wherein the visible marker is visible with an endoscope.

2. The balloon catheter of claim 1, wherein at least one visual marker is in the form of at least one circumferential line around the balloon.

3. The balloon catheter of claim 1, wherein the visual marker is color-coded.

4. The balloon catheter of claim 3, wherein the color of the visual marker indicates the nominal diameter size of the balloon, measured at rated burst pressure.

5. The balloon catheter of claim 1, wherein an outer surface of the balloon at a position of the at least one visual marker is visible, when the balloon is deflated.

6. The balloon catheter of claim 1, wherein an inner surface of the balloon at a position of the at least one visual marker is visible through the proximal tapering portion, when the balloon is inflated.

7. The balloon catheter of claim 1, wherein the at least one visual marker is a combination marker, viewable with visible light and x-ray fluoroscopy.

8. The balloon catheter of claim 1, wherein the at least one visual marker is a combination marker, viewable with visible light and magnetic resonance imaging.

9. The balloon catheter of claim 1, wherein the shaft further comprises an inner member and an outer tubular body; the outer body surrounding at least a portion of the inner member.

10. The balloon catheter of claim 9, wherein the inner member is a wire having proximal and distal ends, the inner member distal end being affixed to the balloon distal portion, and the inner member proximal end being affixed to the hub.

11. The balloon catheter of claim 9, wherein the outer body has at least one reinforcing member extending in a longitudinal direction.

12. The balloon catheter of claim 11, wherein the reinforcing member has high tensile strength.

13. The balloon catheter of claim 12, wherein the reinforcing member is a stainless steel wire affixed to or embedded within a wall of the outer body.

14. The balloon catheter of claim 1, wherein the proximal and distal tapering portions each define an angle with respect to the longitudinal axis, and the angle defined by the proximal tapering portion is steeper than the angle defined by the distal tapering portion.

15. The balloon catheter of claim 14, wherein the angle defined by the distal tapering portion with respect to the longitudinal axis is approximately 45 degrees, and the angle defined by the proximal tapering portion is approximately 80 degrees.

16. The balloon catheter of claim 15, wherein the proximal tapering portion angle is selected to be sufficiently steep that an endoscope positioned proximal of the balloon can view the at least one visual marker through the proximal tapering portion of the balloon.

* * * * *